United States Patent
Sciola et al.

(10) Patent No.: US 11,079,896 B2
(45) Date of Patent: Aug. 3, 2021

(54) INTERACTIVE SYSTEM AND METHOD OF INSTRUMENTING A BIO-MANUFACTURING PROCESS

(71) Applicant: EMD Millipore Corporation, Burlington, MA (US)

(72) Inventors: Laurelle Sciola, Wenham, MA (US); Paul John Ricketts, Oberhaslach (FR); Susan Colt, Winchester, MA (US)

(73) Assignee: EMD MILLIPORE CORPORATION, Burlington, MA (US)

( * ) Notice: Subject to any disclaimer, the term of this patent is extended or adjusted under 35 U.S.C. 154(b) by 249 days.

(21) Appl. No.: 16/061,531

(22) PCT Filed: Oct. 27, 2016

(86) PCT No.: PCT/US2016/059108
§ 371 (c)(1),
(2) Date: Jun. 12, 2018

(87) PCT Pub. No.: WO2017/116543
PCT Pub. Date: Jul. 6, 2017

(65) Prior Publication Data
US 2020/0133460 A1    Apr. 30, 2020

Related U.S. Application Data

(60) Provisional application No. 62/272,415, filed on Dec. 29, 2015.

(51) Int. Cl.
*G06F 3/0481* (2013.01)
*G06F 16/58* (2019.01)
(Continued)

(52) U.S. Cl.
CPC ........ *G06F 3/04815* (2013.01); *G06F 3/0482* (2013.01); *G06F 3/04817* (2013.01);
(Continued)

(58) Field of Classification Search
CPC ............. G06F 3/04815; G06F 3/04817; G06F 3/04845; G06F 3/0482; G06F 16/5866; G06F 2203/04806; G06F 8/34
See application file for complete search history.

(56) References Cited

U.S. PATENT DOCUMENTS 4,004,353 A    1/1977  Valentine
4,622,013 A    11/1986 Cerchio
(Continued)

FOREIGN PATENT DOCUMENTS

CN    102355524 A    2/2012
EP    2290592 A1    3/2011
(Continued)

OTHER PUBLICATIONS

Wu, et al, "An Intelligent Automation Platform for Rapid Bioprocess Design", Journal of Laboratory Automation, vol. 19, No. 4 (Jan. 1, 2014), pp. 381-193, XP002765940, DOI: 10.1177/2211068213499756, Retrieved from the Internet: URL:https://22.ncbi.nlm.nih.gov/pmc/articles/PMC4113973/pdf/10.1177-2211068213499756.pdf; retrieved on Jan. 13, 2017.

(Continued)

*Primary Examiner* — Nicholas Klicos
(74) *Attorney, Agent, or Firm* — Hamilton, Brook, Smith & Reynolds, P.C.

(57) ABSTRACT

Instrumenting or modeling a bio-manufacturing process is disclosed. A data store holds information regarding one or more bio-manufacturing processes. For each process, the data store information includes workflow steps and per step indications of required equipment, services and consumables according to best practice and/or experts. A videographic user interface enables user interactive input regarding a subject bio-manufacturing process from the data store. The user-interface presents a model representation of deployment of the subject bio-manufacturing process. The (Continued)

user interactively navigates and makes selections in the displayed model representation. The user selections include certain bio-manufacturing products, equipment and services from an image database. The images from the image database enable the views of the model representation to appear true to life demonstrating equipment/product layout and physical equipment/computer connections used in the subject bio-manufacturing process. The videographic user interface utilizes various visual effects to guide the user sequentially or logically (and based on best practice and right fit rules) through the steps and pieces of equipment forming the subject bio-manufacturing process.

21 Claims, 12 Drawing Sheets

(51) Int. Cl.
| | | |
|---|---|---|
| *G16B 50/30* | (2019.01) | |
| *G06F 30/20* | (2020.01) | |
| *G06F 3/0482* | (2013.01) | |
| *G06F 3/0484* | (2013.01) | |

(52) U.S. Cl.
CPC ...... *G06F 3/04845* (2013.01); *G06F 16/5866* (2019.01); *G06F 30/20* (2020.01); *G16B 50/30* (2019.02); *G06F 2203/04806* (2013.01)

(56) References Cited

U.S. PATENT DOCUMENTS

| | | | |
|---|---|---|---|
| 4,941,829 A | 7/1990 | Estes et al. | |
| 5,255,207 A | 10/1993 | Cornwell | |
| 5,740,341 A | 4/1998 | Oota et al. | |
| 5,882,204 A | 3/1999 | Iannazo et al. | |
| 6,106,297 A | 8/2000 | Pollak et al. | |
| 6,349,237 B1* | 2/2002 | Koren | B23Q 37/00 |
| | | | 700/96 |
| 6,349,290 B1 | 2/2002 | Horowitz et al. | |
| 6,411,862 B1* | 6/2002 | Hazama | G05B 19/4181 |
| | | | 700/182 |
| 6,701,322 B1 | 3/2004 | Green | |
| 7,058,587 B1 | 6/2006 | Horne | |
| 7,176,949 B1 | 2/2007 | Moser | |
| 2002/0004753 A1 | 1/2002 | Perkowski | |
| 2002/0061743 A1 | 5/2002 | Hutcheson et al. | |
| 2002/0073059 A1 | 6/2002 | Foster et al. | |
| 2002/0077850 A1 | 6/2002 | McMenimen et al. | |
| 2002/0143632 A1 | 10/2002 | Walter et al. | |
| 2003/0028430 A1 | 2/2003 | Zimmerman | |
| 2003/0085921 A1 | 5/2003 | Ghosh et al. | |
| 2003/0155494 A1 | 8/2003 | Olschewski | |
| 2003/0156135 A1 | 8/2003 | Lucarelli | |
| 2003/0233425 A1 | 12/2003 | Lyons et al. | |
| 2004/0006403 A1 | 1/2004 | Bognanno | |
| 2004/0148230 A1 | 7/2004 | Matsui et al. | |
| 2004/0193425 A1 | 9/2004 | Tomes | |
| 2005/0165624 A1 | 7/2005 | Shelton et al. | |
| 2006/0113376 A1 | 6/2006 | Reed et al. | |
| 2006/0137260 A1 | 6/2006 | Shernaman | |
| 2006/0167577 A1 | 7/2006 | Clark et al. | |
| 2006/0172275 A1 | 8/2006 | Cohen | |
| 2006/0178862 A1* | 8/2006 | Chan | G06F 30/00 |
| | | | 703/11 |
| 2007/0027733 A1 | 2/2007 | Bolle et al. | |
| 2007/0050070 A1* | 3/2007 | Strain | G05B 19/4187 |
| | | | 700/99 |
| 2007/0122778 A1 | 5/2007 | Beitel et al. | |
| 2007/0179867 A1 | 8/2007 | Glazer et al. | |
| 2007/0218900 A1 | 9/2007 | Abhyanker | |
| 2007/0240051 A1* | 10/2007 | Sherrill | G06F 3/048 |
| | | | 715/700 |
| 2007/0260432 A1* | 11/2007 | Okada | G06F 30/13 |
| | | | 703/1 |
| 2008/0167947 A1 | 7/2008 | Skinner et al. | |
| 2008/0208702 A1* | 8/2008 | Peterman | G06Q 30/0621 |
| | | | 705/26.5 |
| 2008/0263491 A1 | 10/2008 | Foltz et al. | |
| 2009/0083157 A1 | 3/2009 | Goodman et al. | |
| 2010/0057240 A1* | 3/2010 | Giebels | G06Q 10/06 |
| | | | 700/105 |
| 2010/0120008 A1 | 5/2010 | McDonagh et al. | |
| 2011/0012929 A1 | 1/2011 | Grosz et al. | |
| 2011/0055035 A1 | 3/2011 | Koskay et al. | |
| 2011/0173043 A1 | 7/2011 | Maier | |
| 2011/0213480 A1* | 9/2011 | Zila | G06F 30/13 |
| | | | 700/98 |
| 2013/0041479 A1* | 2/2013 | Zhang | G05B 19/056 |
| | | | 700/17 |
| 2013/0123965 A1 | 5/2013 | Cooper et al. | |
| 2013/0143525 A1 | 6/2013 | Dupler et al. | |
| 2014/0115485 A1 | 4/2014 | Gao et al. | |
| 2014/0282257 A1* | 9/2014 | Nixon | G05B 15/02 |
| | | | 715/835 |
| 2014/0303951 A1* | 10/2014 | Houeto | E21B 43/00 |
| | | | 703/10 |
| 2015/0268469 A1 | 9/2015 | Marsh et al. | |
| 2015/0293529 A1 | 10/2015 | Bardini et al. | |
| 2016/0132046 A1* | 5/2016 | Beoughter | G06F 16/248 |
| | | | 700/17 |
| 2016/0154911 A1* | 6/2016 | Altare | G05B 19/41885 |
| | | | 703/13 |

FOREIGN PATENT DOCUMENTS

| | | | |
|---|---|---|---|
| EP | 2930577 A1 | 10/2015 | |
| GB | 2 192 297 A | 1/1988 | |
| GB | 2 444 748 B | 10/2009 | |
| IN | 3118/CHE/2013 A | 2/2013 | |
| JP | 2003-233473 A | 8/2003 | |
| JP | 2007-520820 A | 8/2006 | |
| JP | 2009-503660 A | 3/2008 | |
| JP | 2010-539600 A | 5/2010 | |
| JP | 2012-008729 A | 1/2012 | |
| JP | 6732028 | 7/2020 | |
| KR | 10-2139609 | 7/2020 | |
| SG | 11201804979 | 1/2021 | |
| WO | 98/02835 A1 | 1/1998 | |
| WO | 01/22341 A1 | 3/2001 | |
| WO | 02/29759 A2 | 4/2002 | |
| WO | 02/054303 A1 | 7/2002 | |
| WO | 2009/146519 A1 | 12/2009 | |
| WO | 2011/004381 A1 | 1/2011 | |
| WO | 2012/075589 A1 | 6/2012 | |

OTHER PUBLICATIONS

International Search Report and Written Opinion for Int'l Application No. PCT/US2016/059108, titled: "Interactive System and Method of Instrumenting a Bio-Manufacturing Process", dated Feb. 2, 2017.
The Audi Configurator—Model, retrieved on [Jan. 22, 2016] http://configurator.audi.co.uk/controller?event-new-conf=1&mandant=accx-uk.
GE Healthcare Life Sciences, retrieved on [Jan. 22, 2016] http://www.gelifesciences.com/webapp/wcs/stores/servlet/HomeView?catalogId=10051&s toreId=11787&langId=-1.
GE Monogram Virtual Kitchen Designer, retrieved on [Jan. 22, 2016] http://www.monogram.com/kitchen-designs/virtual-kitchen/.
Jordan's Furniture, retrieved on [Jan. 25, 2016] https://main.planning wiz.com/jordans.
Nike Air Presto ID, Nike.com, retrieved on [Jan. 24, 2016] http://store.nike.com/us/en_us/product/airprestoid/?piid=41005&pbid=430473609%20%20?pbid=430473609.
Pall Biopharmaceuticals: Biopharmaceutical Products and Technologies, retrieved on [Jan. 22, 2016] http://www.pall.com/main/biopharmaceuticals/biopharmaceuticals-bdb09025.page?.
Sartorius Bioprocess Application Finder, retrieved on [Jan. 22, 2016] https://www.sartorius.com/fileadmin/DID/index.htm.

(56) References Cited

OTHER PUBLICATIONS

Examination Report for Chinese Application No. 201847027572, entitled "Interactive System and Method of Instrumenting A Bio-Manufacturing Process", dated Aug. 5, 2020.

* cited by examiner

12

| | |
|---|---|
| PROCESS 1 . . . | ~18a |
| FORMAT TYPE: SINGLE USE → (su) | |
| MULTI USE → (mu) | ~15 |
| WORKFLOW SEQUENCE OF STEPS (su) <br> ------- <br> WORKFLOW SEQUENCE OF STEPS (mu) | ~19 |
| STEP 1: EQUIPMENT/COMPONENTS RELATED → EQUIP. <br>     SERVICES <br>     SCALING EQUIPMENT → EQUIP. <br>     AUXILIARY EQUIPMENT | ~20a |
| STEP 2: EQUIPMENT/COMPONENTS RELATED → EQUIP. <br>     SERVICES <br>     SCALING EQUIPMENT → EQUIP. <br>     AUXILIARY EQUIPMENT | ~20b |
| . . . | |
| STEP n: EQUIPMENT/COMPONENTS RELATED → EQUIP. <br>     SERVICES <br>     SCALING EQUIPMENT → EQUIP. <br>     AUXILIARY EQUIPMENT | ~20n |
| . . . | |
| PROCESS n . . . | ~18n |

FIG. 1B

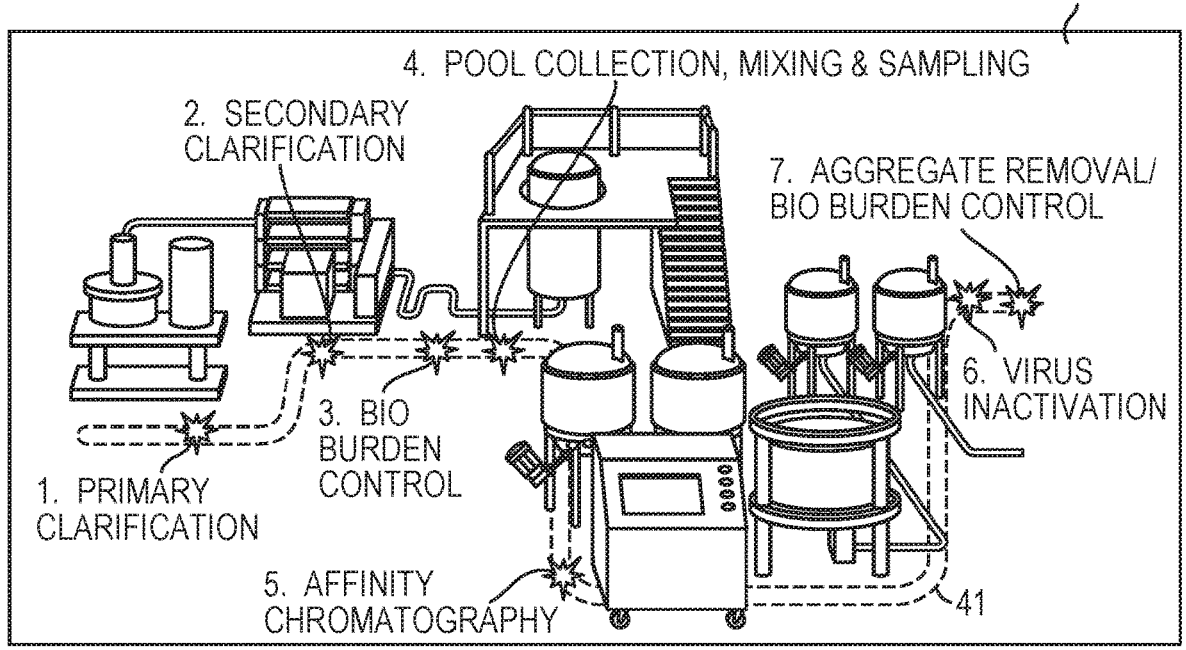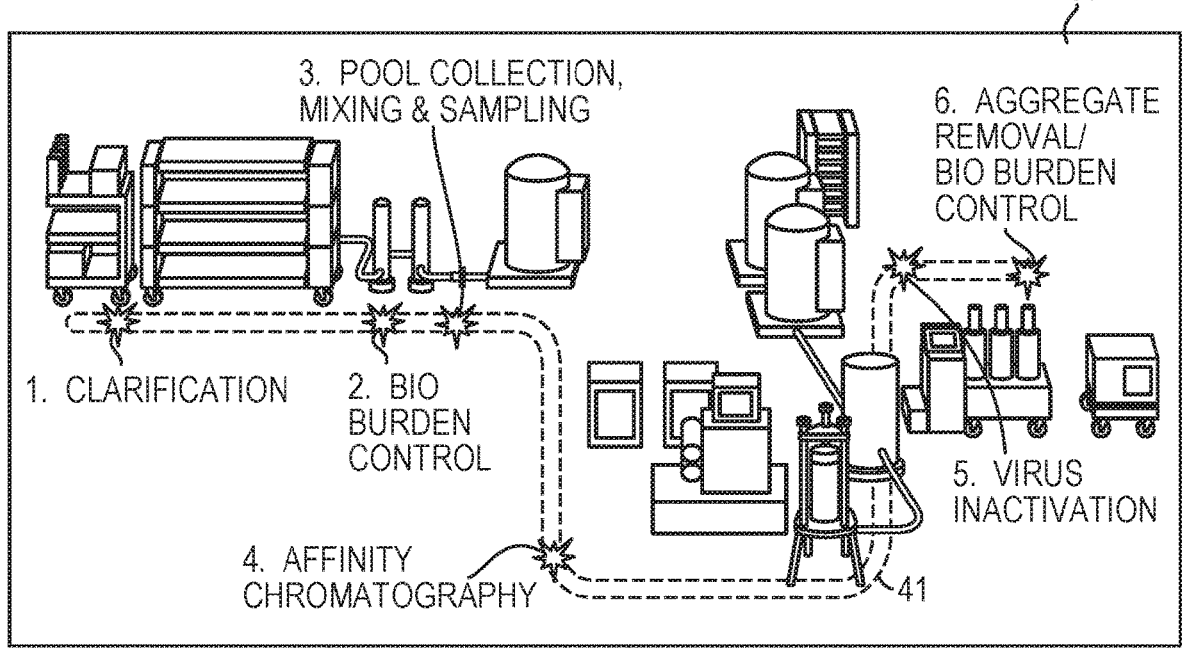
FIG. 3A

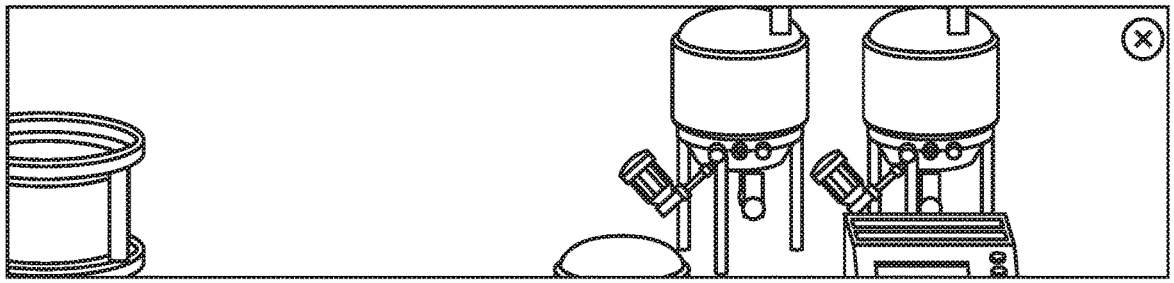

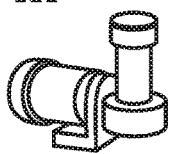 < Back to Purification

Polishing Chromatography
NovAseptic® GMP Mixer
· Wide product range with complete solutions for superior mixing
· Engineered for optimal performance, reliability, durability and easy of maintenance performance
· Complies with the most stringent cleanability and sterilizability requirements. All models are completely cleanable - and sterilizable-in-place (CIP/SIP)

Available Scales
· up to 30000 L

☆ Favorites
⚙ Customization Available
◉ Recommended Chemicals

Resources

 NovAseptic® Nixed Brochure

 NovAseptic® Mixer, Drive Unit, GMP Data Sheet

Related Products

 Series 30000™ Single-Round Housing

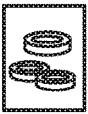 NovAseptic® Connectors

Related Services

· Column Packing Services
· Installation & Qualification Services for K-Prime Chromatography System
· Installation & Qualification Services for IsoPack® Chromatography System
· Installation & Qualification Services for Slurry Transfer Skid NovAseptic Connectors

FIG. 5B

FROM 17

| Favorites | |  | My Process |  |
|---|---|---|---|---|
| Name | Step | | Name | Process |
| Mobius® Single-Use Mixing System | Mixing and Prep | View > | Name | Process |
| Mobius® FlexReady Solution for Buffer and Media Preparation | Sterile Filtration | View > | Tom1 | Buffer Prep | View > |

FIG. 6

INTERACTIVE SYSTEM AND METHOD OF INSTRUMENTING A BIO-MANUFACTURING PROCESS

RELATED APPLICATIONS

This application is the U.S. National Stage of International Application No. PCT/US2016/059108, filed on Oct. 27, 2016, published in English, which claims the benefit of U.S. Provisional Application No. 62/272,415, filed on Dec. 29, 2015. The entire teachings of the above application(s) are incorporated herein by reference.

BACKGROUND

Current methods to obtain information on bio-manufacturing products (equipment) and company capabilities are accessed today through a variety of sources. Typical sources of such information include: product catalogues, application guides, company websites, presentations at conferences and trade shows, and correspondence by company representatives using face to face, phone or email methods. These resources must be used in combination for a user to gain a complete perspective of a company's portfolio and capabilities.

For instance, a user looking to select products, services and equipment for a biopharmaceutical process starts by visiting a company's website to browse what that company offers. If the user sees products of interest, the user may follow up with a company sales representative, either by phone or email to receive answers to questions and/or to obtain advice. This process is time consuming and involves a user accessing multiple web site pages to search for product information which either partially exists or may be missing entirely. As a user navigates into web site pages to access detailed product information he is taken further away from the Home (Capabilities Overview) page, and is commonly dead ended at an external (disconnected/expired link) page. As can be seen by the examples below, various company web sites do not easily or readily provide in one spot, information to help a user decide what product types, sizes or categories are needed to build a useful bio-manufacturing process. This lack of complete and holistic process and application information and access to technical advice (best practice) requires the user to take additional steps to seek additional sources of information, typically obtain feedback from a company technical expert or representative, and may even require direct testing which is time consuming and inefficient.

In contrast to a web site product catalogue or a product/service based application guide, direct contact with a company representative typically provides more relevant and targeted information to address a user's needs. However, such contact with a company representative still results in a delay as the representative searches for and then sends the requested materials. Time zone differences and language barriers can add to the time delay.

EXAMPLES www.sartorius.us

This website shows a series of process areas (e.g., media prep, cell culture, cell harvest, etc.) within a selected application area (e.g. monoclonal antibodies "mAb", Buffer, Media, and Final Fill). The website shows a 2-D representation of a product they sell which is applicable for the process step. The website does not provide context for the application area or infrastructure needed to choose appropriate products for the process step, nor does the website provide any information or logic rules to help a user choose the best (right fit) product, decide product scale, process type (single use or multi-use), or indicate how products should be connected and used together.

The website is not interactive and does not support the ability to build a process or to customize process workflow. The website also lacks logic rules (built-in technical advice) to help a user select a "right fit" product from a catalogue list based on experience/best practices.

A user cannot explore an actual production process workflow, or visualize how products could be connected and used together.

www.pall.com

This website is not interactive and lacks any integrated organized workflow functionality. The website utilizes a vertical layout of products, organized by product line, and does not address customer application/use scenarios. The website sporadically provides product support documentation, however this information is not conveniently organized by application area or as a customer would intuitively use them—at one's fingertips (i.e., at the point of need). Only a few pages of the website provide product support documentation. Instead, each page of the website presents blocks of text with a mixture of product technologies, application areas and services. There is also no visual representation of a process workflow or overall capabilities.

The website does not support the ability to build a process or to customize products. The website's "Selection Guide" is a text only listing of required items. The text makes no reference to particular products, and gives no description of application.

www.gelifesciences.com

Relative to the two previous websites, this website is easier to navigate. However, this website does not organize the company's products and services by application area or process workflow. In contrast, the website is organized by product line and technology area only (e.g., upstream, downstream, single-use and services). The website uses four technology areas to categorize product groups. When one of the four main areas is selected by a user, the user is brought to a landing page. The landing page lists different product technologies, but does not provide to the user a view of the producer's processing capabilities. Further, the website does not link product offerings to a pharmaceutical manufacturing process by application or process workflow step, and products and product support documentation are not conveniently organized by application or as a customer would intuitively use them (i.e., at the point of need).

SUMMARY OF THE INVENTION

There is a need and desire for a user to be able to: (i) view and quickly explore a process flow, and (ii) have all the information immediately and conveniently available in one place, at each step of the process. The information is needed in sufficient depth and detail to allow a user to take the next step in the buying, or at least decision making process. Thus, the information needs to include product/equipment sizes and product types (e.g., capsules, cartridges, etc.), product/equipment performance recommendations, and process types and/or available process scale/sizing options (e.g., single use, multi-use; for scale at R&D levels, production levels, pilot levels, etc.) and describe/build awareness of product and process customization options.

Applicants provide a computer method, apparatus, and system that addresses the shortcomings of the industry and fulfills the foregoing needs.

Applicant's computer method, apparatus and system give a user the ability to (i) build a fully functioning biopharmaceutical/bio-manufacturing process train (complete workflow), (ii) specify the products (equipment, consumables, and components) used in it, and (iii) specify preference on the type of process (single-use, multi-use, or hybrid). Embodiments also include the ability to customize individual products used in the process or workflow. As such, embodiments enable a user to create a customized process train which the user can save, send and share with others. Embodiments show all steps and products (equipment) required in the process workflow to successfully execute the unit operation and the entire overall process.

Within embodiments a user also has the ability to contact a technical specialist to ask questions and solicit advice on a specific product (equipment, components, consumables, and/or accessories) or process step.

Another aspect of Applicant's computer method, application and system is the speed, convenience and ease of access to relevant information (for a customer facing sales, application and technical collateral) at a user's fingertips at the point of need in the viewing and buying process.

Embodiments provide computer-implemented method, apparatus and system of instrumenting a bio-manufacturing process. The computer method, apparatus, and system comprise: (a) a data store holding in computer memory information regarding bio-manufacturing processes, and (b) a user interactive video graphic interface. For each process, the data store information includes: (i) a description of the sequence of steps that form the workflow of the bio-manufacturing process, and (ii) per step, indications of equipment and services that support the step according to best practice and expert technical experience. In some embodiments, the data store information further includes supporting media/collateral to help a user choose and/or use the products.

In some embodiments, one or more processors are coupled to host or access the data store and an image database. The image database stores digital images of certain bio-manufacturing equipment (may be brand or manufacturer specific). For each piece of certain bio-manufacturing equipment, the image database has digital images of different views of that piece of equipment (e.g., top, front, back, side, bottom, perspective(s), isometric views, etc.). The image database supports 3D image display, 3D animations, video clips, audio clips, and/or other display of the pieces of the certain bio-manufacturing equipment, components, related (or associated) consumables, and/or corresponding services. The processors associate equipment indicated in the data store with corresponding images of the bio-manufacturing equipment in the image database.

In some embodiments, a computer, such as a client computer, in communication with the one or more processors executes the video graphic user interface and enables user interactive input regarding a subject bio-manufacturing process from the data store. In some embodiments, the subject bio-manufacturing process may be of a particular type, per therapeutic area or molecule type. The user interface displays a model representation of a hypothetical bio-manufacturing facility deploying the subject bio-manufacturing process. In one embodiment, the user interface provides various screen views of a working model illustrating a generic set of equipment in a typical (or general) equipment configuration (layout and interconnections) for implementing the bio-manufacturing process. The displayed model representation/working model may be navigated under user control through the user-interface. Some embodiments allow the user the ability to telescope in/out for greater/lesser product (equipment) detail and information.

Importantly, the user interface interactively displays various views of the model representation/working model in a manner that provides to the user: (i) an overview of candidate pieces of equipment and corresponding services for the subject bio-manufacturing process, the candidate pieces of equipment being from the image database, (ii) a layout of equipment from the image database and corresponding services required to execute a given step in the subject bio-manufacturing process based on best practice/expert technical experience, and (iii) a sense of scale, relationship, utility and physical connections between pieces of equipment used in the subject bio-manufacturing process.

User input through the user interface results in a set of user-selected (and specified) pieces of equipment, services and/or process consumables from the image database that carries out the subject bio-manufacturing process at the scale and process type (single use, multi-use, or hybrid) specified by the user and according to best practice as determined by the processors from the data store information. In this way, embodiments visualize and instrument (including right-fit specific equipment to) a bio-manufacturing process in an efficient, informative and convenient manner to suit the end-user.

The bio-manufacturing processes include biopharmaceutical or similar processes that produce vaccines, plasma, blood products, monoclonal antibodies, antibody fragments, stem cells, antibody drug conjugates, allergenics, gene therapeutics, or biosimilar drugs.

In the displayed model representation/working model, at each of the process steps for the subject bio-manufacturing process, the user interface highlights step-appropriate equipment and corresponding services (i.e. "right fit" recommendations and process step recommendations). Such highlighting, in turn, prompts and enables the user to efficiently make appropriate selection of certain pieces of bio-manufacturing equipment, services and/or process consumables. In embodiments, the user-interface highlights include user-interactive (selectable) pulsating beacons, and user-interactive (selectable) color-coded icons.

In embodiments, the user interface enables the user to specify or otherwise configure each step of the subject bio-manufacturing process as employing single use or multi-use pieces of equipment (referred to as a single use or multi-use process type). In this way, the subject bio-manufacturing process may be customized to optionally be of a hybrid process format having single use equipment at one or more steps and multi-use equipment at other steps in the process.

In some embodiments, the one or more processors hosting or accessing the data store execute logic rules that (1) ensure equipment compatibility across the set of user selected and specified pieces of certain bio-manufacturing equipment, and (2) match user-selected/specified equipment with best practice and expert indicated pieces of equipment of the data store. For non-limiting example, for the user specified combination of multi-use and single use pieces of equipment, the logic rules ensure that only rational and viable combinations are constructed. The logic rules also ensure viability of the workflow configuration resulting from the user's equipment selection and specification.

Further, in some embodiments, the processors adjust size of a candidate piece of equipment as a function of user-specified scale of the subject bio-manufacturing process. In particular, size of a candidate piece of equipment may be based on production volume and/or volume throughput of the subject bio-manufacturing process as specified by the user. The user interface enables the user to specify a volume (e.g., approximate, projected, or the like).

According to some embodiments, the user interface as supported by the image database individually displays views including 3D views, videos, animations, and the like of the candidate pieces of equipment. Further, the user interface enables the user to selectively telescope (zoom) in and out the displayed views of the candidate pieces of equipment. Similarly the user interface enables the user to selectively rotate or otherwise orient a candidate piece of equipment in some displayed views. The telescoping and rotating viewing options, under user control, provide the additional levels of information and view per piece of equipment as well as for overall product range and capabilities of the candidate pieces of equipment (for the subject bio-manufacturing process) as the user needs.

In embodiments, the user interface highlights related pieces of equipment in the subject bio-manufacturing process or otherwise visually illustrates relationships between displayed pieces of equipment. For non-limiting example, the highlighted related pieces of equipment may be color coded. The user interface also displays/illustrates how the related pieces of equipment interact and connect to each other.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 1A-1C are a block diagram and schematic views of one embodiment of the present invention.

FIGS. 3A and 3B are screen view illustrations of candidate pieces of equipment for a process step in a subject bio-manufacturing process in the user interface of FIG. 2.

FIGS. 4, 5A and 5B are illustrations of further screen views in the user interface of FIG. 2 providing user-friendly prompts, zoom/telescoping features, and access to additional information upon user request.

FIG. 6 is a screen view of further output of the user interface of embodiments.

DETAILED DESCRIPTION OF THE INVENTION

A description of example embodiments of the invention follows.

The teachings of all patents, published applications and references cited herein are incorporated by reference in their entirety.

By way of overview, embodiments of the present invention provide a computer-based tool for visualizing and modeling a subject bio-manufacturing process during user instrumentation of the same. The tool enables a user to navigate through a video graphic representation of a hypothetical, pertinent manufacturing facility meanwhile prompting the user for selection and specification of relevant equipment and various components (parts, accessories, consumables, and/or service agreements) for implementing (and "right-fitting" equipment to) the subject bio-manufacturing process according to best practice and expert technical experience. In response to user input, the tool (i) interactively configures a best practice set of equipment (as a function of user selection and specification), and (ii) generates a virtual model of the workflow (through the configured set of equipment) of the subject bio-manufacturing process to scale of operation as specified by the user.

Figure 1A:
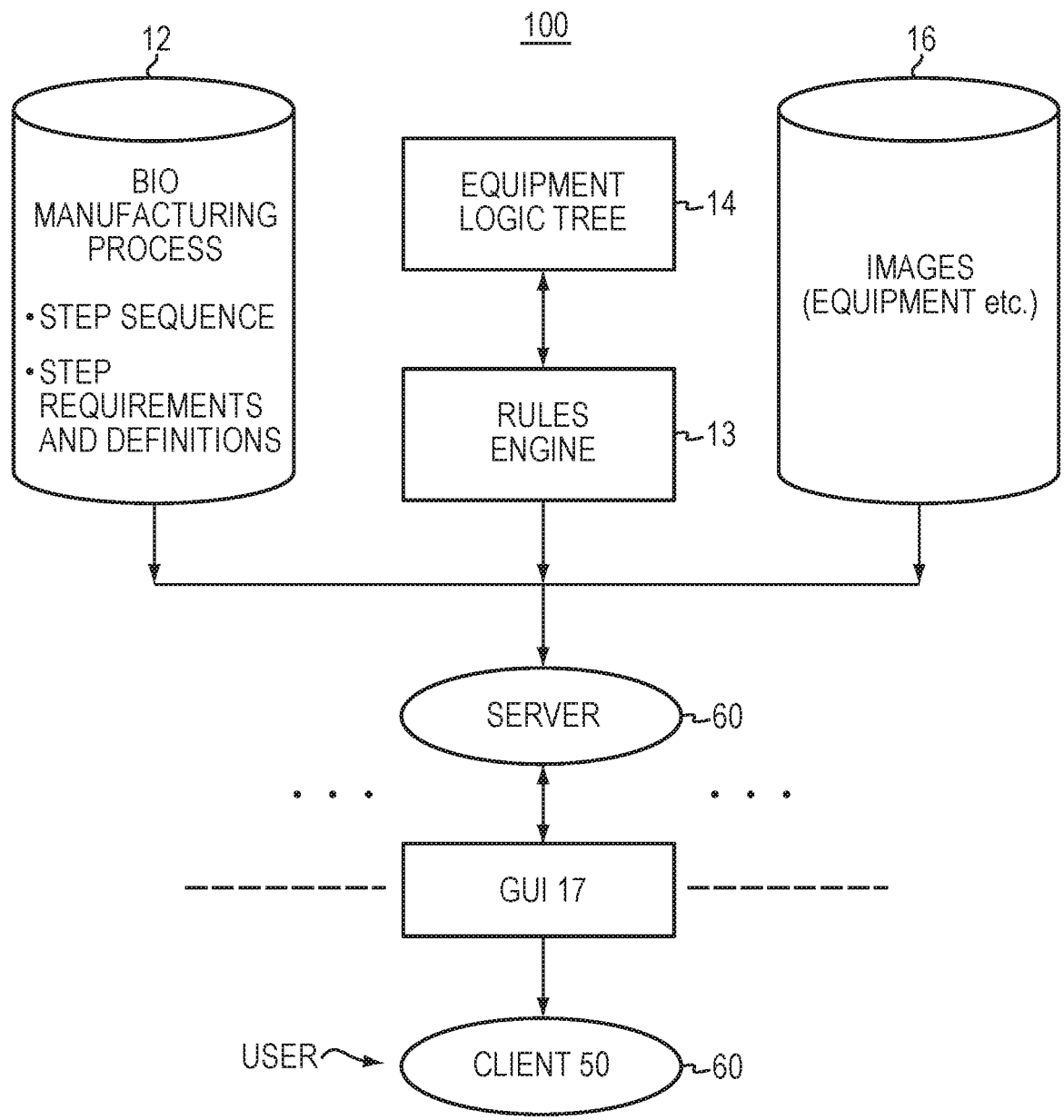

In particular, as illustrated in FIG. 1A, tool 100 comprises (a) a data store 12 in a computer memory, and (b) a user-interactive video graphic interface (GUI) 17. In some embodiments, the data store 12 holds in computer memory information regarding various bio-manufacturing processes, biopharmaceutical processes and the like. Non-limiting examples include processes that produce vaccines, plasma, blood products, antibody drug conjugates, monoclonal antibodies (mAb), antibody fragments, stem cells, allergenics, gene therapeutics, or bio-similar drugs. In some embodiments, for each process, the data store 12 holds information regarding (i) the sequence of steps that form or defines the workflow of the bio-manufacturing/biopharmaceutical process, and (ii) per step, the equipment and services that support the step according to best practice and/or expert technical experience.

FIG. 1B illustrates a data store 12 employed in embodiments of the present invention. According to some embodiments, for each bio-manufacturing or bio-pharmaceutical process represented in tool 100, the data store 12 has a respective record 18a, b, . . . n (18 generally). In a given record 18, there is information regarding the corresponding process information such as process format type (e.g., single use, (typically of plastic which is disposed of after use), multi-use (typically of stainless steel which is cleaned and reused) or hybrid (typically a combination of single use and multi-use with typically one format type per piece of equipment or process step)) 15 and the workflow sequence of steps 19, 20 a, b . . . n (generally 20) of the process. The record 18 may have a description 19 of the workflow for a single use process format and a description 19 of the workflow for a multi-use format.

In some embodiments, for each step 20, the record 18 describes equipment, components, services, accessories, and consumables, or equivalent products for implementing and supporting the step according to best practice and/or expert technical experience. The record 18 includes a scaling factor for determining equipment size as a function of user-specified scale of operation. Operation or process scale may be for example at R&D levels, production levels, pilot levels, and the like. The record 18 may also indicate auxiliary or related equipment per step 20.

Figure 1C:
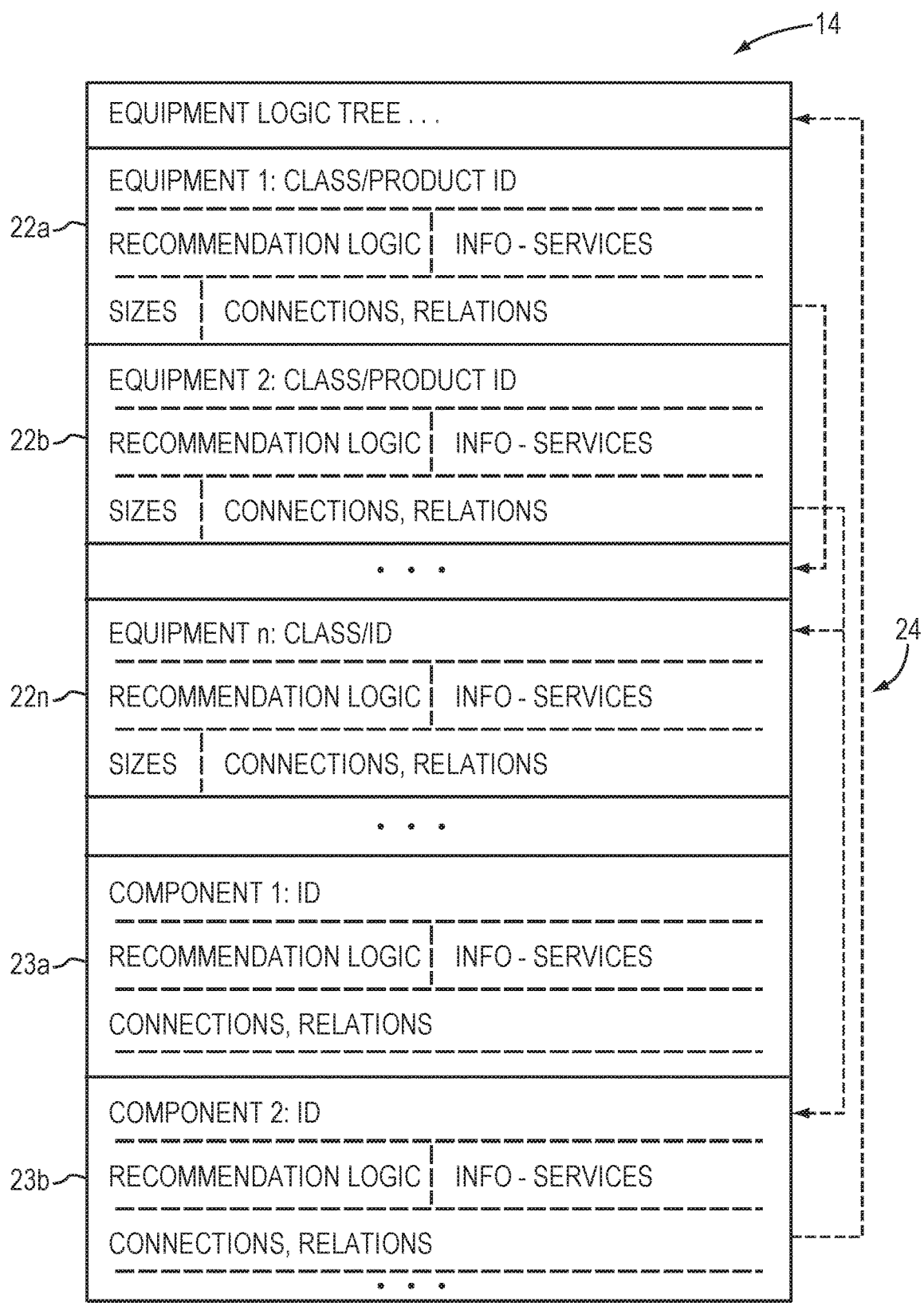

In a preferred embodiment, the process record 18 description of equipment, components and related pieces of equipment is populated from an equipment logic tree 14 (shown in FIGS. 1A and 1C). The equipment logic tree 14 has a different record or entry 22, 23 (shown as 22a, b . . . n, 23 a, b . . . n for ease of understanding) for each of the various pieces of equipment and components utilized in the bio-manufacturing/bio-pharmaceutical processes of tool 100. In a given equipment entry 22, the class, available sizes and product identifier of the piece of equipment is indicated. The given entry 22 also provides recommendation logic (i.e., logic rules) that uses best practice and/or expert technical experiences, and determines when to recommend use of the piece of equipment and defines which services and related products should be shown. Service (and other) information is recorded in or linked to the tree entry 22 for the respective piece of equipment. Connections to and relationships among the different pieces of equipment and components with respect to the given piece of equipment of a tree entry 22 are indicated by links, pointers, or the like 24. In this way, equipment logic tree 14 provides a hierarchy or map of sorts of the compatible pieces of equipment and components and allowable/feasible connections and logical workflow in process operations.

According to some embodiments, component entries 23 similarly provide respective product ID, recommendation logic (i.e., logic rules), and service (or other) information of a corresponding component. Pointers 24 to/from a component entry 23 similarly provide logic-based connections and relationships of the corresponding (or associated) component among the different pieces of equipment and other components.

Returning to FIG. 1A, in some embodiments one or more processors 60 access the data store 12 and image database 16 and execute Rules engine 13 to support or otherwise operate the video graphic user interface 17. In some embodiments, the image database 16 stores digital images, 3D images, and the like of certain bio-manufacturing equipment and products. The equipment and products may be of different brands and manufacturers. For each piece of equipment and products, the image database 16 has digital images of different views of that piece of equipment/product. For example, the different views may include a top or plan view, front view, back view, side views, bottom view, various perspective views, isometric views, and so forth. The image database 16 supports 3D image renderings, videos, 3D views, life-like/realistic process renderings, animations, and/or other types of displays of the different pieces of equipment and products. The processors 60 associate equipment indicated in the data store 12 with corresponding images of the bio-manufacturing equipment in the image database 16.

According to some embodiments, Rules engine 13 when executed by processor 60 applies the Rules (logic rules) of the data store 12 process records 18 to make recommendations of equipment, components, consumables, and accessories, and to determine various factors or features (e.g., equipment size, workflow compatibility, etc.) per bio-manufacturing process 18 and process step 20. In particular, processor 60 responds to user input through user interface 17 and makes determinations based on best practice and expert techniques as programmed in the logic rules of data store 12 process records 18 illustrated next with reference to FIGS. 2-5B. The examples illustrated through FIGS. 2-5B are for purposes of illustration and not limitation of Applicant's invention.

Figure 2:
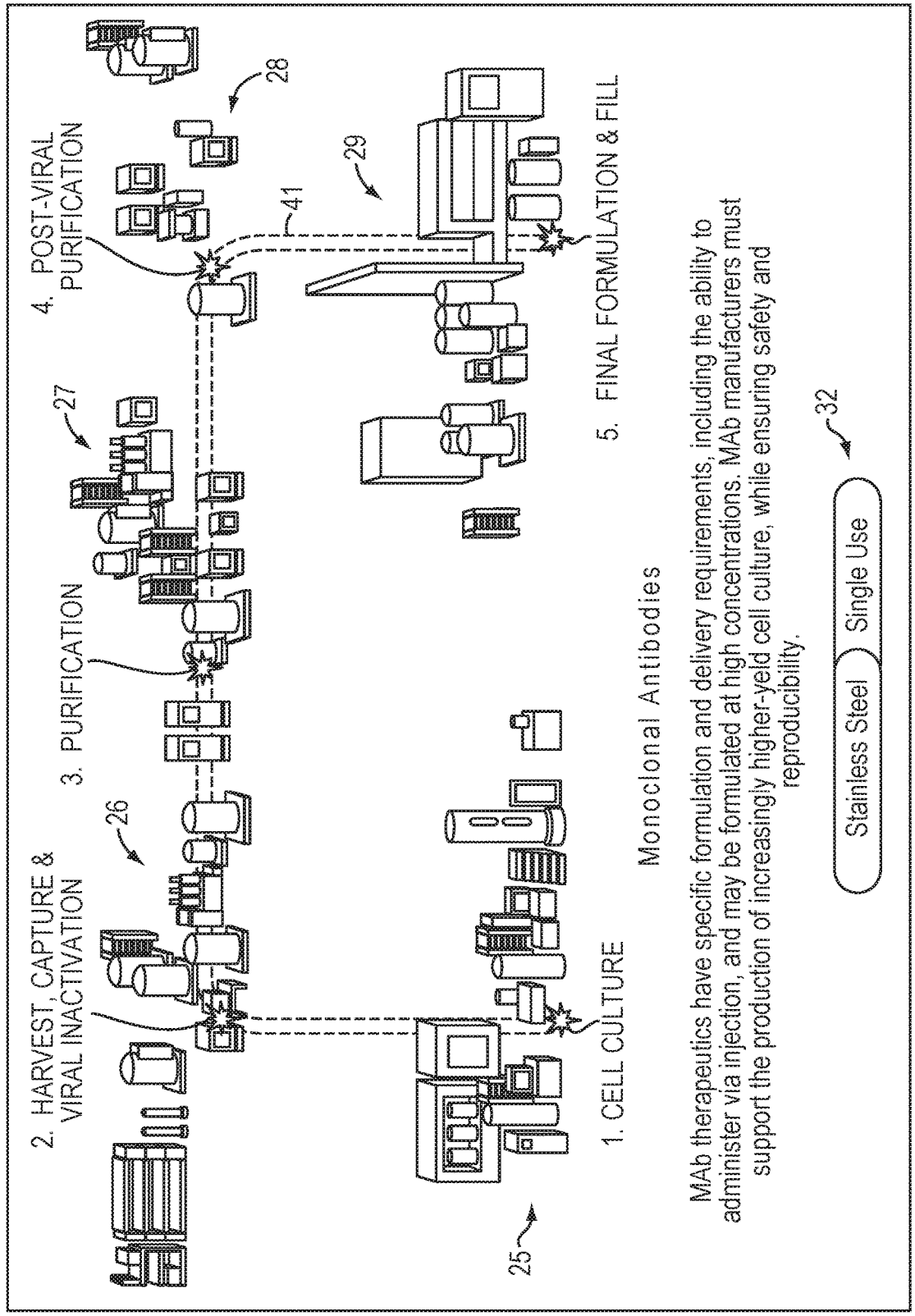
FIG. 2 is a screen view illustration of a hypothetical bio-manufacturing facility rendered in the user interface of an embodiment of the present invention. The hypothetical facility displays pertinent equipment to carry out bio-manufacturing processes.

In some embodiments, client or user computer 50 executes user interface 17 and video graphically renders a user-interactive illustration (or model representation) of a user navigable bio-manufacturing facility. The bio-manufacturing facility may be hypothetical and generic, but is illustrated as having pertinent equipment for implementing a bio-manufacturing process of the user's choosing from the data store 12. In some embodiments, the different illustrated pieces of equipment are user interactive (i.e., selectable, view enhanceable by telescoping, rotating, etc.) using video or imaging technology, video gaming techniques, and the like. For each of the different bio-manufacturing processes of data store 12, the user interface 17 illustrates a different respective user-interactive layout of equipment, process consumables and services required to execute each step of the bio-manufacturing process according to best practice and/or expert technical experience determined by processors 60 from data store 12 information. In this way, tool 100 serves as an interactive, integrated 3D bio-manufacturing process workflow model that provides to the user: (i) an overview of equipment (products) and service capabilities by application, (ii) a useful layout of equipment (products), consumables and services required to execute each step of a subject bio-manufacturing process based on best practice and/or expert technical experiences determined by processors 60 from data store 12 information, and (iii) a sense of scale, relationship, and physical connections between pieces of equipment used in the subject bio-manufacturing process. FIG. 2 is illustrative and a non-limiting example.

In FIG. 2, the video graphic user interface 17 shows a hypothetical bio-manufacturing facility deploying a typical set of equipment configured for manufacturing monoclonal antibodies and antibody drug conjugates (the subject bio-manufacturing process selected by the user and at the process scale specified by the user, for example). The model representation of the bio-manufacturing facility rendered by the user interface 17 is user-navigable. That is, the user is able to "explore" the displayed facility and under user command move or otherwise navigate through the illustrated process workflow to access different rooms and process steps 25, 26, 27, 28, 29. In some embodiments, at each process step 25, 26, 27, 28, 29, the user interface 17 presents pertinent equipment, collateral, process consumables, and/or services sized for the step location and scale of operations specified by user input. That is, from data store 12 information, processor 60 responsively generates "right fit" equipment recommendations and process step 25, 26, 27, 28, 29 recommendations for display through user interface 17. In some embodiments, the user interface 17 presents or otherwise displays a virtual pathway 41 to visually guide the user through the workflow of the sequential process steps 25, 26, 27, 28, 29. The pathway 41 visually leads the user between sequential process steps 25-29, as well as through parts of each step 25-29. This is accomplished by the supporting data store 12, equipment logic tree 14 and Rules engine 13 as previously described.

Highlighting and/or other visual effect techniques are employed in rendering virtual pathway 41. For example, in one embodiment blinking or flashing beacons (shown as animated star shapes, dots or circles in FIGS. 2-4) illuminate along pathway 41 at the process steps 25, 26, 27, 28, 29 and at the various pieces of equipment of a respective process step. The flashing beacons and illuminated pathway 41 assist the user in properly and efficiently working (logically progressing) through the subject bio-manufacturing process workflow of the displayed facility. In this way, the user interface 17 helps the user to:

i) better visualize a subject (user-selected) bio-manufacturing process, ii) more logically approach making decisions on equipment and consumables per process step, and iii) interactively design or model, in part, and instrument (including "right fit") the pertinent bio-manufacturing facility according to best practice and/or expert technical experience.

The following is a non-limiting example of a bio-manufacturing process to produce monoclonal antibodies (mAb). In some embodiments, the Rules engine 13 is executed by processor 60 to apply the logic rules from the respective process record 18 (in this instance, the process record corresponding to the production of mAb) from the data store 12. The Rules engine 13, applying the logic rules, is able to make right fit and best practice recommendations of the equipment, components, consumables, and accessories, and to determine various factors or features (e.g., equipment size, workflow compatibility, etc.) required to produce the amount of product specified or entered by the user.

Continuing with the non-limiting example, the user inputs or otherwise can select a desired production amount (e.g. 5 kg) of drug product. The Rules engine 13, applying the logic rules from the respective process record 18, determines in order to produce the user requested/specified 5 kg of drug product, a 2000 L bioreactor (~2.5 g/L titer) will be required. Rules engine 13 also determines the approximate sizing and process type (single-use, multi-use or hybrid system) needed to perform the process step. For example, a 2000 L bioreactor (~2.5 g/L titer) is to be harvested with (31 m2 of) depth filtration media (20 m2 primary clarification, 11 m2 secondary clarification) and pooled in a 2000 L mixer. The Rules engine 13 together with equipment logic tree 14 may also determine alternative equipment, components, consumables, and/or accessories to accomplish a process step 20 of respective record 18. As a result of each determination, Rules engine 13 and user interface 17 render user interactive video-graphic displays of images of pertinent pieces of equipment from image database 16. In this example, a centrifuge could be used in lieu of the primary clarification step. The Rules engine 13 continues to apply the logic rules from the respective process record 18 (and supported by equipment logic tree 14 and image database 16) to complete the video graphic and user-interactive illustration (display) of the rest of the workflow for the production of mAb as follows.

Next, the clarified filtrate would undergo the capture chromatography step (with 32 L of protein A resin for 4 cycles), and then held at low pH for virus inactivation (in two 2000 L mixers in series); any resulting aggregates would be removed with depth filtration (1.1 m2) or capsule filters (4.5 m2), and pooled for feed to purification chromatography operated in bind-elute mode. Rules engine 13 and user interface 17 display each of these pieces of equipment, accessories and consumables to the user in turn. Next, (approximately 32 L of) cation exchange resin would be needed, operated at 3 cycles and then pooled for polishing chromatography. This typically requires (19 L of) anion exchange resin, operated for 1 cycle in flow-through mode. Next, viral clearance would require approximately 1.55 m2 of membrane; the ~400 L of filtrate would be fed to a Tangential Flow Filtration (TFF) system with 9 m2 of 30 kDa regenerated cellulose membrane, resulting in 50 L of concentrated mAb that could be filtered through 0.7 m2 of sterilizing-grade polyvinylidene fluoride (PVDF) or polyethersulfone (PES) membrane and held for final formulation additions and redundant sterile filtration through two stacked-disk capsule filters (~total 1 m2). Rules engine 13 and user interface 17 display user-interactive views of each of these parts (connected in sequence and in context detail) for the subject bio-manufacturing process.

In this way, client or user computer 50 executes user interface 17 and video-graphically renders a user-interactive illustration (or model representation) of a user navigable bio-manufacturing facility having the foregoing pertinent equipment for implementing the example bio-manufacturing process to produce mAb.

According to some embodiments, the user interface 17 enables a user to customize his preference of equipment and processing technology (single-use or multi-use) via a toggle button 32 while retaining process utility and functionality. The ability to customize equipment/product selection, process type, and/or processing scale leverages the embedded logic rules to ensure cross product (equipment) compatibility and to ensure that the resulting process workflow construct is rational and efficient. User interface 17 provides toggle button 32 at the overall process level of FIG. 2 to enable the user to specify the subject bio-manufacturing process as multi-use (typically of stainless steel which is cleaned and reused) or single use format (typically of plastic which is disposed of after one use).

Figure 3B:
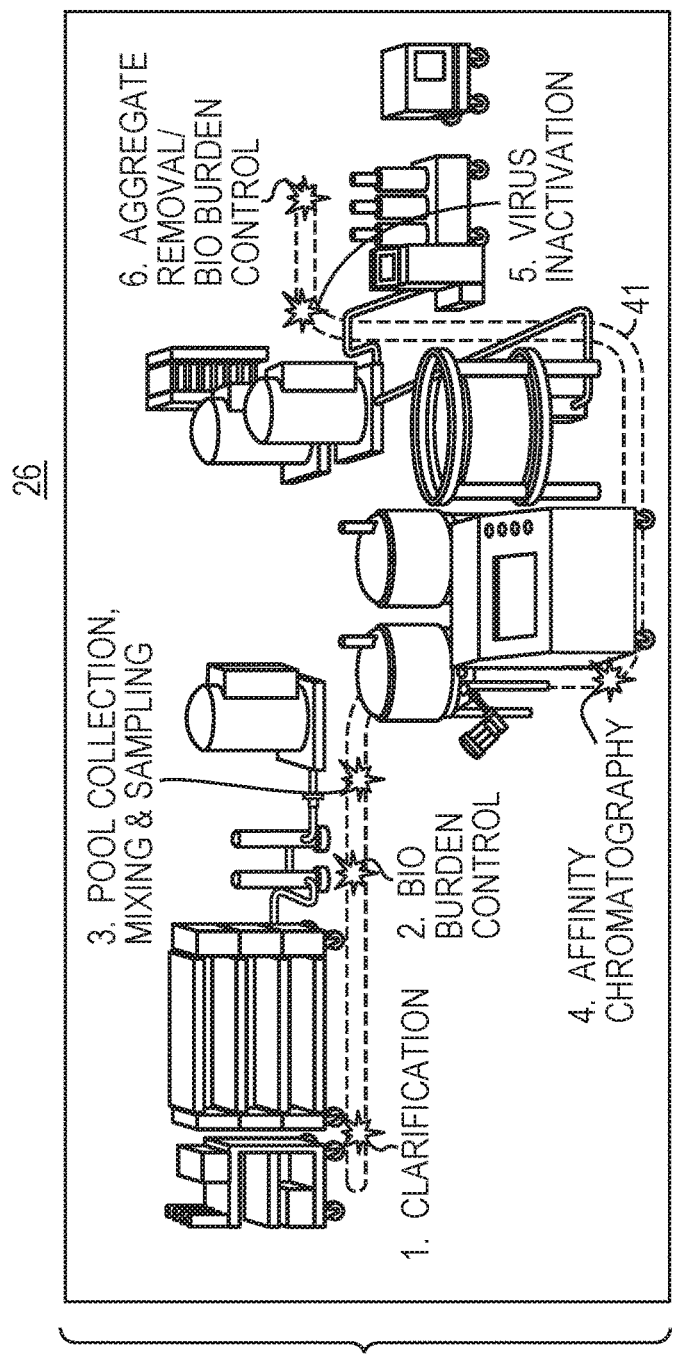

In some embodiments, the user interface 17 also provides toggle button 32 at individual process steps such as demonstrated in FIGS. 3A-3B for step 26. For non-limiting example, if the user selects (via button 32) a process type of multi-use for step 26, the user interface 17 (employing images from image database 16) updates the screen view to show a step appropriate multi-use (Stainless Steel) configuration of equipment and services. In some embodiments, this is accomplished by user interface 17 being supported by the server 60 executing Rules engine 13. Updated screen view 26a is illustrative. If and when the user selects (via button 32) the single use process type for step 26, tool 100 and the user interface 17 updates the screen view to show step appropriate equipment and services for a single use format of the process step 26 as shown in 26b of FIGS. 3A and 3B. If undecided, the user can easily toggle between the two process formats (single use, multi-use) with a touch of a button/toggle button 32, and the user interface 17 (tool 100) responds with screen view updates accordingly.

Where each process step 25, 26, 27, 28, 29 can be user configured individually and separately to be of single use process format or multi-use process format, the subject bio-manufacturing process (the monoclonal antibody fabrication process in the example of FIG. 2) may result in a hybrid combination of process formats. Logic rules are executed by server 60 in response to such user input through user interface 17 to ensure that only rational and viable combinations are constructed.

Figure 4:
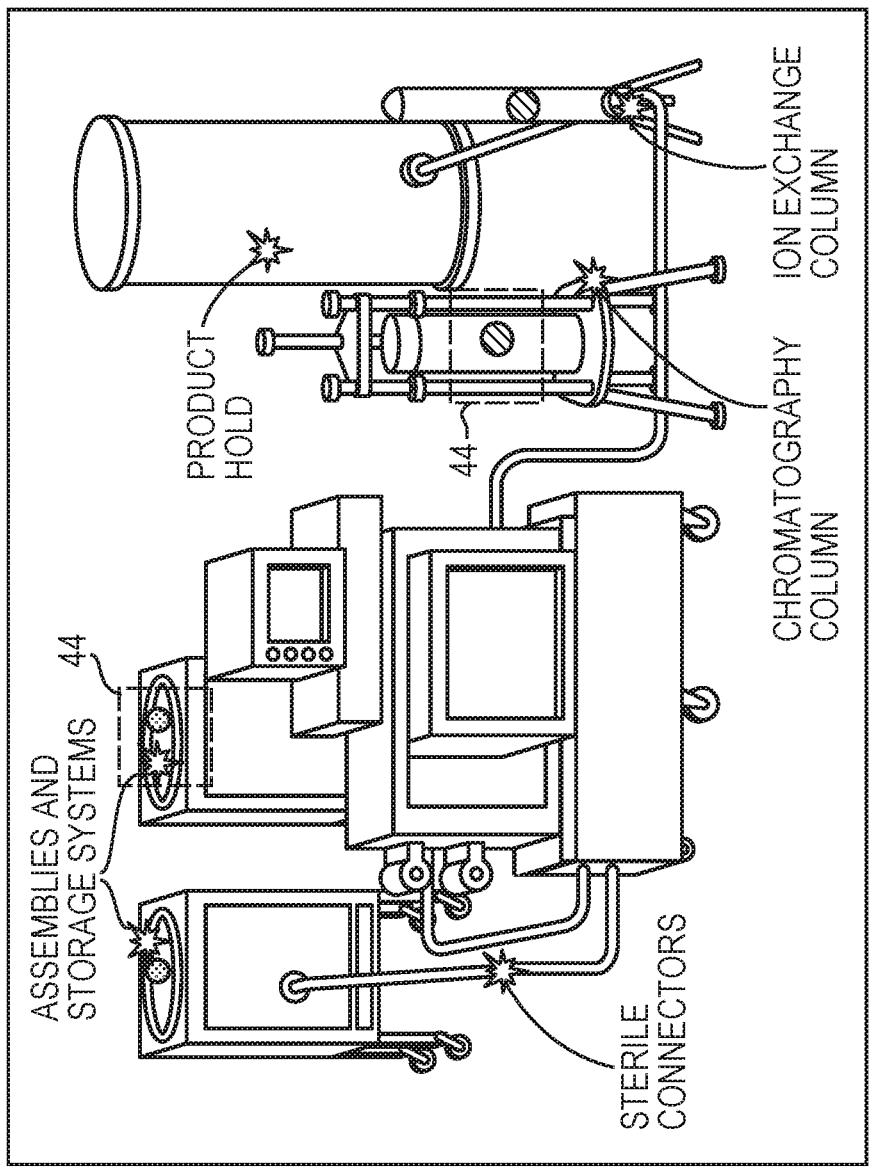

Tool 100 and user interface 17 provide the user a clear demonstration of overall bio-manufacturing process and individual process step capabilities with equipment (products), consumables and services integrated into true to life workflow context. According to some embodiments, at each process step 25, 26, 27, 28, 29, only step appropriate systems (equipment), services, consumables and collateral are highlighted as shown in FIG. 4 for step 27. The user interface 17 (as supported by Rules engine 13 determinations) shows how the pieces of equipment are connected to each other and how related parts interact. Color-coding or other visual schemes for indicating and displaying relationships of parts may be employed. In embodiments, the various pieces of equipment, especially application specific consumables, are easily accessed in user interface 17 via pulsating beacons and color-coded click-able (user interactive) icons 44 shown in FIG. 4.

Figure 5A:
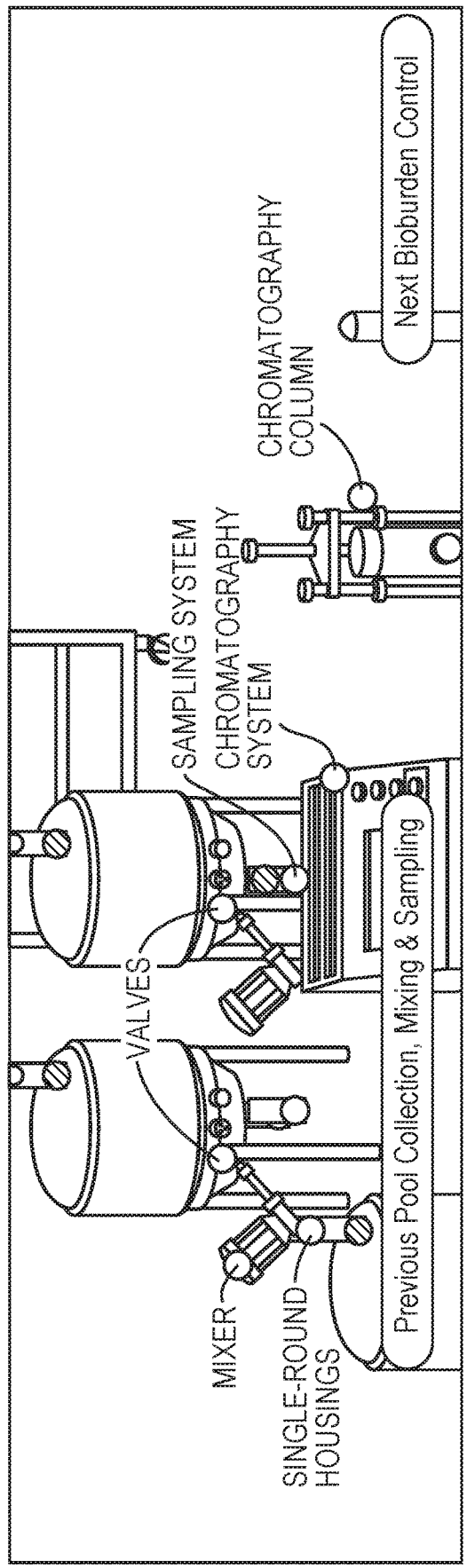

In some embodiments, the user interface 17, as supported by server 60 and image database 16, enables a user to telescope in and out of displayed screen views to gain a deeper view and detail of equipment pieces and parts or to step back to view overall product range and capabilities. Known or common magnifying or zooming technology and techniques may be utilized. FIGS. 5A-5B are illustrative.

In FIGS. 5A and 5B, a screen view of example process step 29 as displayed by user interface 17 is shown. In some embodiments, the different displayed elements (equipment pieces, parts and components with dot icons) are user interactive meaning upon user command, the user interface 17 telescopes in/out, rotates/orients displayed images, provides additional information, and the like. In some embodiments, tool 100 (specifically equipment logic tree 14 and/or data store 12) compiles all relevant product information (e.g., datasheets, validation documents, user guides, technical briefs, application notes, animations, and interactive guides) and conveniently locates this information at a user's point of need to advance user decision making. In the non-limiting example of FIG. 5A-5B, the user selects (clicks on) the GMP mixer icon of process step 29, and user interface 17 (supported by server 60) responsively renders the additional information (lower boxes of FIGS. 5A, 5B) regarding the mixer in an updated screen view.

Tool 100 enables a user to save results of a user session, including the foregoing user interactions, selections, specifications and/or other input by the user. The saved results (a customized set of equipment for a subject bio-manufacturing process) can be made a "Favorite", sent, saved, and/or shared with others, etc. through operating system functions common in computer networks. FIG. 6 is illustrative. The tool's 100 save/share functionality facilitates communication across geographies, languages and time zones allowing information to be shared efficiently between process engineers (internally and externally). Tool 100 also enables users to directly access a sales, technical or customer service representative through communications operations common in computer networks as made apparent in FIGS. 7 and 8.

Computer Support

Figure 7:
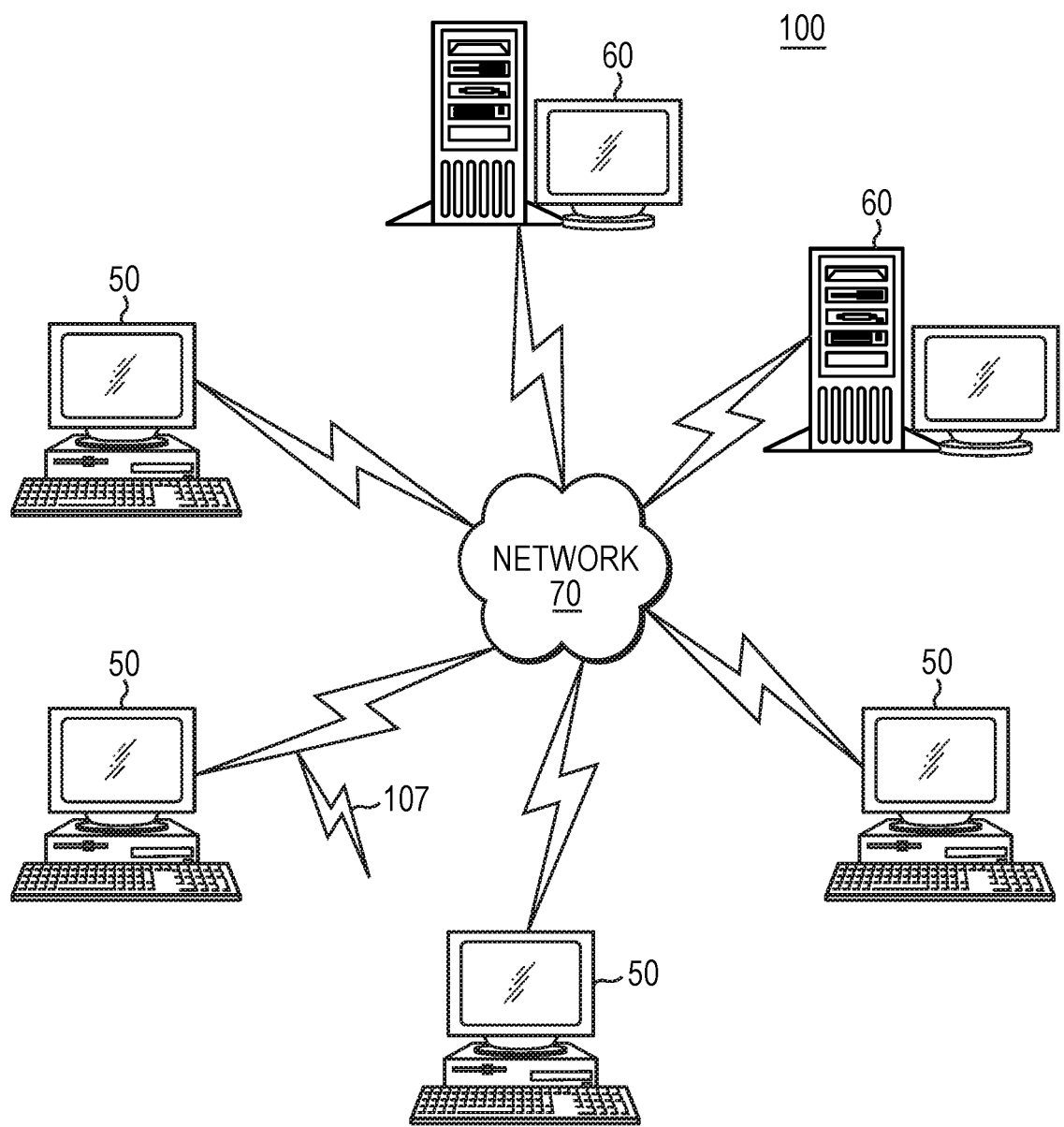
FIG. 7 is a schematic view of a computer network embodying the present invention.

FIG. 7 illustrates a computer network or similar digital processing environment in which the present invention may be implemented.

Client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), a worldwide collection of computers, Local area or Wide area networks, cloud computing, and gateways that currently use respective protocols (TCP/IP, Bluetooth, etc.) to communicate with one another. Other electronic device/computer network architectures are suitable.

Figure 8:
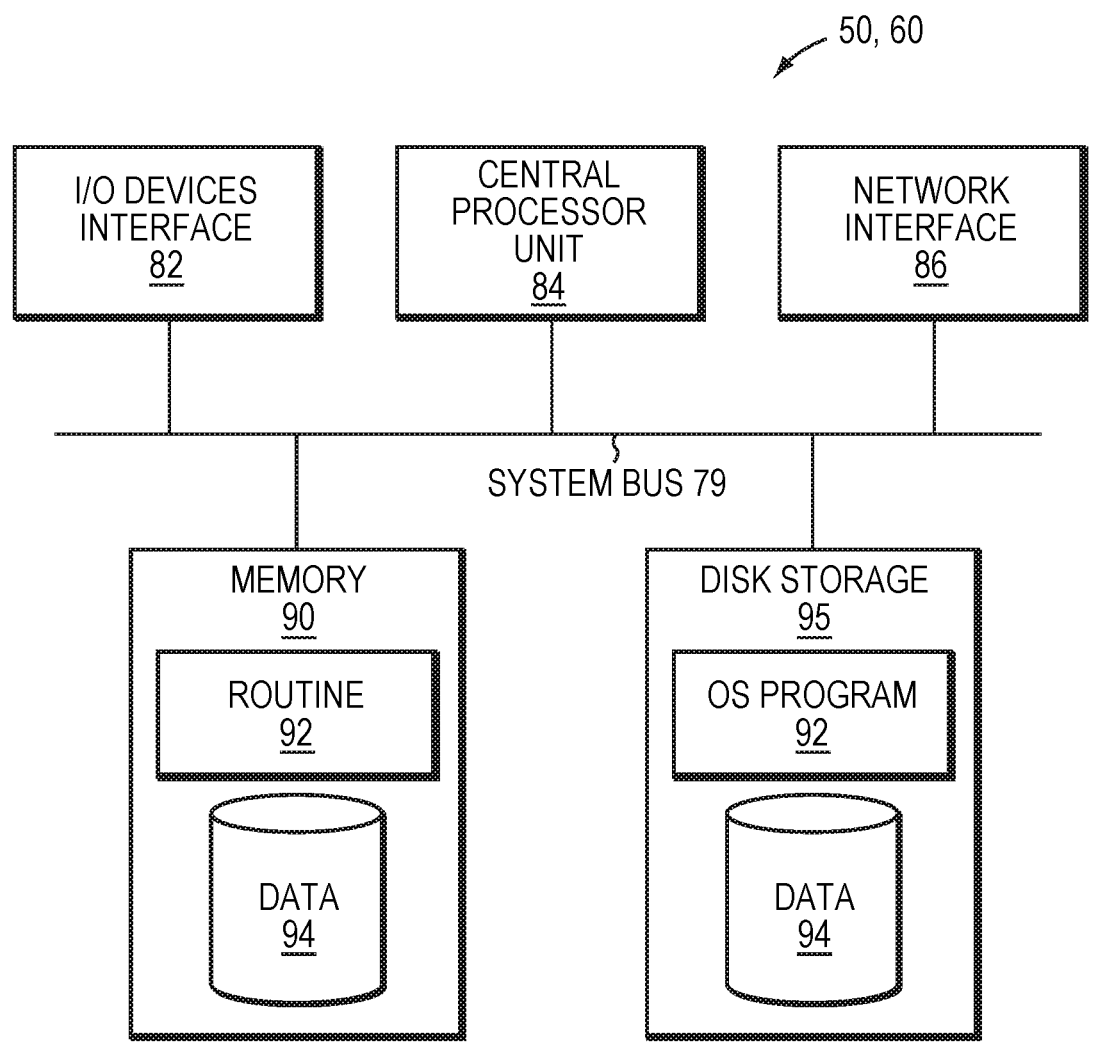
FIG. 8 is a block diagram of a computer node in the computer network of FIG. 7.

FIG. 8 is a diagram of the internal structure of a computer (e.g., client processor/device 50 or server computers 60) in the computer system of FIG. 7. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 7). Memory 90 provides volatile storage for computer software instructions 92 and data 94 used to implement an embodiment of the present invention (e.g., program code for tool 100, user interface 17 and supporting software processing 900 detailed above and below). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network (s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

Figure 9:
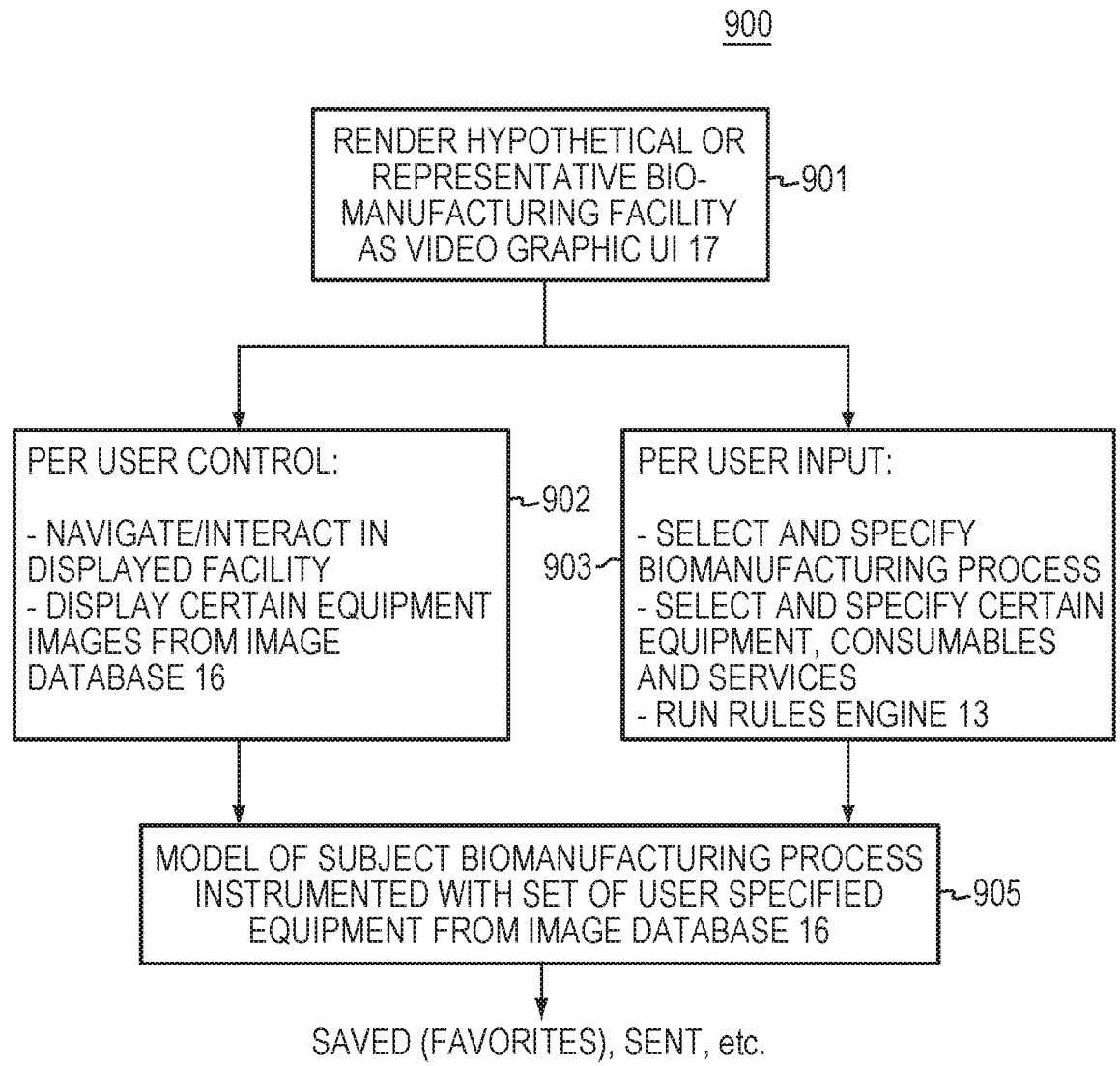
FIG. 9 is a flow diagram of embodiments.

FIG. 9 is a flow diagram 900 of embodiments of the present invention. Computer routine or procedure 900 supports user interface 17 and operations thereof as described above. In particular, at step 901, computer routine 900 renders a representative illustration of a hypothetical bio-manufacturing facility in user interface 17. The non-limiting representative illustration is a video graphic model responsive to user interaction therewith. For non-limiting example, under user control (command) step 902 navigates through model views of the facility, toggles views between multi-use and single use per user selection, and displays various images (magnified, rotated, changed perspective) of certain equipment from image database 16. Similarly step 903, in response to user input, (i) selects and specifies a subject biomanufacturing process, and (ii) selects and specifies certain equipment (including sizing, as function of user specified scale of operation) and services per step of the subject bio-manufacturing process. Step 903 also executes the Rules engine 13 for the various rules described above including per bio-manufacturing step determining best practice, expert techniques, and right fit equipment/services/consumables from data store 12 information.

The output of routine 900 is a virtual model 905 of the user selected subject bio-manufacturing process instrumented with a best practice and/or right fit set of certain user-specified equipment from image data base 16 for carrying out or otherwise implementing the subject bio-manufacturing process. The virtual model 905 or defining set of user specified equipment may be saved in computer memory, sent (shared) with other network users, and/or otherwise stored (archived, etc.).

While this invention has been particularly shown and described with references to example embodiments thereof, it will be understood by those skilled in the art that various changes in form and details may be made therein without departing from the scope of the invention encompassed by the appended claims.

For example, the foregoing described animated dots or circles along pathway 41 at the process steps 25, 26, 27, 28, 29 may be emanating concentric circles, flashing beacon lights, siren lights or of other eye-catching (attention getting) construction. Various graphical arts techniques can be employed to implement such aspects of the pathway 41.

What is claimed is:

1. A computer system for instrumenting a bio-manufacturing process, comprising:
    A) a data store in computer memory and holding information regarding one or more bio-manufacturing processes, for each process, the information including:
        i) a sequence of steps forming workflow of the bio-manufacturing process, and
        ii) per step indications of equipment and services supporting the step, including best practice information, relating to various factors or features required to produce an amount of product specified or entered by a user;
    B) one or more processors coupled to access the data store and an image database and to execute a rules engine to operate a video graphic user interface, the image database storing digital images of certain bio-manufacturing equipment, for each of the certain pieces of bio-manufacturing equipment, the image database having digital images of different views of the piece of bio-manufacturing equipment, and the processors associating equipment indicated in the data store with corresponding images of the bio-manufacturing equipment in the image database, the rules engine applying logic rules to make right fit and best practice recommendations for equipment, components, consumables, and accessories; and
    C) the video-graphic user-interface executed by a computer in communication with the one or more processors and enabling user interactive input regarding a user selected subject bio-manufacturing process from the data store, the user-interface displaying a model representation of a hypothetical bio-manufacturing facility deploying the subject bio-manufacturing process, the displayed model representation being navigated under user-control, and the user-interface interactively displaying various views of the model representation in a manner that provides to a user:
        i) an overview of candidate pieces of equipment and corresponding services for the subject bio-manufacturing process, the candidate pieces of equipment being from the image database,
        ii) a layout of equipment from the image database and corresponding services required to execute a given step in the subject bio-manufacturing process as determined by the processors applying the best practice information from the data store information, wherein based on user selection at each process step, the rules engine determines alternative equipment, components, consumables, and/or accessories to accomplish a process step, and as a result of each determination render user interactive video-graphic displays of images of pertinent pieces of equipment from image database, and
        iii) a sense of scale, relationship, and physical connections between pieces of equipment used in the subject bio-manufacturing process,
        the user input resulting in a display of a set of recommended equipment from the image database for carrying out the subject bio-manufacturing process, the set determined by the one or more processors applying the best practice information from the computer memory, and wherein the user interface as supported by the image database displays individual views of the candidate pieces of equipment, and enables the user to selectively telescope (zoom) in and out of displayed views of the candidate pieces of equipment.

2. A computer system as claimed in claim 1 wherein the one or more bio-manufacturing processes include individual bio-pharmaceutical processes that produce: vaccines, plasma, blood products, monoclonal antibodies, antibody fragments, stem cells, antibody drug conjugates, allergenics, gene therapeutics, or bio-similar drugs.

3. A computer system as claimed in claim 1 wherein:
    the one or more processors determine, from the data store information, equipment recommendations and bio-manufacturing process step recommendations according to the best practice information; and
    at each of the process steps for the subject bio-manufacturing process in the displayed model representation, the user interface highlights step appropriate equipment, pertinent collateral and corresponding services enabling the user to make appropriate selection of the certain pieces of equipment for the subject bio-manufacturing process.

4. A computer system as claimed in claim 3 wherein the highlights include user-interactive pulsating beacons and user-interactive color-coded icons.

5. A computer system as claimed in claim 1 wherein the user interface enables the user to specify each step of the subject bio-manufacturing process as having a single use or multi-use equipment, optionally resulting in the subject bio-manufacturing process being of a hybrid process format.

6. A computer system as claimed in claim 5 wherein the one or more processors execute logic rules that ensure: cross equipment compatibility, and resulting workflow configuration viability.

7. A computer system as claimed in claim 1 wherein the one or more processors adjust sizing of the candidate equipment as a function of user-specified scale of the subject bio-manufacturing process.

8. A computer system as claimed in claim 7 wherein sizing of the candidate equipment is based on volume to be handled by the subject bio-manufacturing process.

9. A computer system as claimed in claim 1 wherein the views of the candidate pieces of equipment include 3D views or renderings.

10. A computer system as claimed in claim 1 wherein the user interface highlights related pieces of equipment in the subject bio-manufacturing process and displays how the related pieces of equipment interact and connect to each other.

11. A computer system as claimed in claim 10 wherein the highlighted related pieces of equipment are color coded.

12. A computer-based method of modeling a bio-manufacturing process, comprising:
storing in computer memory information regarding one or more bio-manufacturing processes, for each process, the information including:
i) a sequence of steps forming workflow of the bio-manufacturing process, and
ii) per step indications of equipment and services supporting the step according to best practice and/or experts, relating to various factors or features required to produce an amount of product specified or entered by a user;
accessing with one or more processors the computer memory information and an image database, the image database holding digital images of certain bio-manufacturing equipment, for each of the certain pieces of bio-manufacturing equipment, the image database having digital images of different views of the piece of bio-manufacturing equipment, and the processors associating equipment indicated in the computer memory information with corresponding images of the bio-manufacturing equipment in the image database;
receiving from a user a selected subject bio-manufacturing process;
executing a rules engine to operate a video graphic user-interface;
applying logic rules to make right fit and best practice recommendations for equipment, components, consumables, and accessories for the bio-manufacturing process; and
providing a video-graphic user-interface executed by a computer in communication with the one or more processors and enabling user interactive input regarding the subject bio-manufacturing processes, the user-interface displaying a model representation of a hypothetical bio-manufacturing facility deploying the subject bio-manufacturing process, the displayed model representation being navigated under user-control, and the user-interface interactively displaying various views of the model representation in a manner that provides to a user:
i) an overview of candidate pieces of equipment and corresponding services for the subject bio-manufacturing process, the candidate pieces of equipment being from the image database,
ii) a layout of equipment from the image database and corresponding services required to execute a given step in the subject bio-manufacturing process according to best practice and/or expert technical experience, wherein based on user selection at each process step, the rules engine determines alternative equipment, components, consumables, and/or accessories to accomplish a process step, and as a result of each determination render user interactive video-graphic displays of images of pertinent pieces of equipment from image database, and
iii) a sense of scale, relationship, and physical connections between pieces of equipment used in the subject bio-manufacturing process,
the user input resulting in a display of a set of recommended user-selected equipment from the image database for carrying out the subject bio-manufacturing process according to best practice as determined by the one or more processors from the computer memory information, wherein the user interface as supported by the image database displays individual views of the candidate pieces of equipment, and enables the user to selectively telescope (zoom) in and out of displayed views of the candidate pieces of equipment.

13. A computer-based method as claimed in claim 12 wherein the one or more bio-manufacturing processes include individual bio-pharmaceutical processes that produce: vaccines, plasma, blood products, monoclonal antibodies, antibody fragments, stem cells, antibody drug conjugates, allergenics, gene therapeutics, or bio-similar drugs.

14. A computer-based method as claimed in claim 12 further comprising: at each of the process steps for the subject bio-manufacturing process in the displayed model representation, highlighting in the user interface step appropriate equipment and corresponding services enabling the user to make appropriate selection of the certain pieces of equipment for the subject bio-manufacturing process.

15. A computer-based method as claimed in claim 14 wherein said highlighting includes employing user-interactive pulsating beacons and user-interactive color-coded icons.

16. A computer-based method as claimed in claim 12 wherein the user interface enables the user to specify each step of the subject bio-manufacturing process as having a single use or multi-use equipment, optionally resulting in the subject bio-manufacturing process being of a hybrid process format.

17. A computer-based method as claimed in claim 16 wherein the one or more processors execute logic rules that ensure: cross equipment compatibility, and resulting workflow configuration viability.

18. A computer-based method as claimed in claim 12 wherein the one or more processors adjust sizing of the candidate equipment as a function of user-specified scale of the subject bio-manufacturing process.

19. A computer-based method as claimed in claim 18 wherein sizing of the candidate equipment is based on a volume to be handled by the subject bio-manufacturing process.

20. A computer-based method as claimed in claim 12 wherein the views of the candidate pieces of equipment include 3D views or renderings.

21. A computer-based method as claimed in claim 12 wherein the user interface visually highlights related pieces of equipment in the subject bio-manufacturing process and displays how the related pieces of equipment interact and connect to each other.

* * * * *